（12）United States Patent
Doll et al.

(10) Patent No.: US 9,243,147 B2
(45) Date of Patent: Jan. 26, 2016

(54) COLOR TRAVEL OXIDIZED ALUMINUM PIGMENTS (71) Applicants: Jonathan Doll, Cincinnati, OH (US); Jennifer Louis, Cincinnati, OH (US); Kenneth Fields, II, Cincinnati, OH (US)

(72) Inventors: Jonathan Doll, Cincinnati, OH (US); Jennifer Louis, Cincinnati, OH (US); Kenneth Fields, II, Cincinnati, OH (US)

(73) Assignee: Sun Chemical Corporation, Parsippany, NJ (US)

( * ) Notice: Subject to any disclaimer, the term of this patent is extended or adjusted under 35 U.S.C. 154(b) by 0 days.

(21) Appl. No.: 14/419,744

(22) PCT Filed: Aug. 8, 2013

(86) PCT No.: PCT/US2013/054097
§ 371 (c)(1),
(2) Date: Feb. 5, 2015

(87) PCT Pub. No.: WO2014/025977
PCT Pub. Date: Feb. 13, 2014

(65) Prior Publication Data
US 2015/0197640 A1    Jul. 16, 2015

Related U.S. Application Data (60) Provisional application No. 61/753,457, filed on Jan. 17, 2013, provisional application No. 61/681,681, filed on Aug. 10, 2012.

(51) Int. Cl.
*A01N 59/06*    (2006.01)
*C09C 1/64*     (2006.01)
*A61K 33/06*    (2006.01)
(Continued)

(52) U.S. Cl.
CPC . *C09C 1/644* (2013.01); *A61K 8/26* (2013.01); *A61K 33/06* (2013.01); *A61K 33/08* (2013.01); *A61Q 19/00* (2013.01); *C08K 9/10* (2013.01); *C09C 1/64* (2013.01); *C09C 1/642* (2013.01); *C09C 1/648* (2013.01); *A61K 2800/43* (2013.01); *B22F 2303/20* (2013.01); *B22F 2304/15* (2013.01); *C01P 2006/63* (2013.01); *C01P 2006/64* (2013.01); *C01P 2006/66* (2013.01)

(58) Field of Classification Search
CPC .................. B22F 2303/20; B22F 2304/15
See application file for complete search history.

(56) References Cited

FOREIGN PATENT DOCUMENTS

WO    WO 96/38505    12/1996

OTHER PUBLICATIONS

International Search Report dated Nov. 27, 2013 for Application No. PCT/US2013/054097.
(Continued)

*Primary Examiner* — Carlos Azpuru
(74) *Attorney, Agent, or Firm* — Frost Brown Todd LLC (57) ABSTRACT The oxidized aluminum pigment comprises not more than 95% by weight metallic aluminum, wherein the pigment is a flaky particle, and has a color travel from the hue angle range of about 50° to about 100° at the aspecular observation angle of 15° to a hue angle range of about 200° to about 270° at the aspecular observation angle of 110°. The oxidized aluminum pigment may be made by the steps of: providing a flaky aluminum pigment, and oxidizing the aluminum pigment in a water-in-oil emulsion comprising a surfactant in the presence of a base. The water-in-oil emulsion comprises a mixture of water dispersed in a hydrocarbon solvent. The aluminum pigment is predominantly in the hydrocarbon solvent during the oxidation step, and the amount of water in the mixture is in the range of about 5% to about 40% of the total weight of the emulsion.

20 Claims, 4 Drawing Sheets (51) Int. Cl.
*A61K 33/08* (2006.01)
*A61K 8/26* (2006.01)
*A61Q 19/00* (2006.01)
*C08K 9/10* (2006.01)

(56) References Cited

OTHER PUBLICATIONS

Greiwe, K., et al., "A New Class of Aluminum Pigment", Paint and Ink International, Redhill, GB, vol. 10, No. 4, Jul. 1, 1997, 3pgs.

COLOR TRAVEL OXIDIZED ALUMINUM PIGMENTS

CROSS REFERENCE TO RELATED APPLICATIONS

The present application hereby claims the benefit of PCT/US2013/054097, filed on Aug. 8, 2013, which claimed benefit of the provisional patent applications entitled "COLOR TRAVEL OXIDIZED ALUMINUM PIGMENTS," Ser. No. 61/681,681, filed on Aug. 10, 2012, and Ser. No. 61/753,457, filed on Jan. 17, 2013, the disclosures of which is hereby incorporated by reference in their entirety.

BACKGROUND

Aluminum flake pigments have potential to be used in a variety of applications such as coatings and cosmetics, among others. Aluminum pigments are advantageous as they give coated objects a silvery metallic sheen, have a light to dark color travel, have good sparkle, excellent hiding power and are extremely light and weather fast. Moreover, by blending with different organic or inorganic pigments, different colors with a metallic effect can be achieved.

However, blending traditional organic pigments with aluminum has some drawbacks. Most importantly, some of the metallic character is lost due to increased scattering by the organic pigment particles. Having a colored aluminum pigment where the flake is colored would be advantageous as the metallic character can be preserved. Unfortunately, many of the strategies used to color aluminum are laborious, requiring complicated and/or dangerous procedures and potentially toxic precursors. Other strategies used to color aluminum, such as direct attachment of a pigment to the aluminum surface, suffer from a number of drawbacks, including an inability to achieve deep colors, poor adhesion of the pigments to the aluminum surface, and a reduction of lightfastness of organic pigments on the aluminum surface. The last of these issues is caused by the fact that organic pigments are essentially exposed to more light; the incoming light and the light reflected by the surface of the aluminum.

BRIEF SUMMARY

The oxidized aluminum pigment comprises not more than 95% by weight metallic aluminum, wherein the pigment is a flaky particle, and has a color travel from the hue angle range of about 50° to about 100° at the aspecular observation angle of 15°, to a hue angle range of about 200° to about 270° at the aspecular observation angle of 110°. The pigment may be used in a variety of applications including, but are not limited to: coatings, such as interior and exterior decorative coatings (for wood, plastic and other substrates), varnish, lacquer, paint, powder coating, coil coating, industrial coating, protective and maintenance coatings, architectural coatings, automotive coating (such as refinish, OEM, interior and wheel coatings); inks such as lithographic, lithographic offset, flexographic, energy curable inks, gravure, writing ink, and screen ink; colored concrete; seed coatings; as a colored inclusion in plastics, glass, ceramics; textiles; and cosmetics, including, mascara, nail lacquer, eye shadow, eye liner, foundation, concealers, hair gel, hair spray, shampoo, lotions, blush, rouge, and soaps.

The oxidized aluminum pigment may be made by the steps of: providing a flaky aluminum pigment, and oxidizing the aluminum pigment in a water-in-oil emulsion comprising a surfactant in the presence of a base. The water-in-oil emulsion comprises a mixture of water dispersed in a hydrocarbon solvent. The aluminum pigment is predominantly in the hydrocarbon solvent during the oxidation step, and the amount of water in the mixture is in the range of about 5% to about 40% of the total weight of the emulsion.

BRIEF DESCRIPTION OF THE FIGURES

The accompanying drawings, which are incorporated in and constitute a part of this specification, illustrate embodiments, and together with the general description given above, and the detailed description of the embodiments given below, serve to explain the principles of the present disclosure.

FIG. 1: Scanning electron microscope (SEM) micrographs of the pigments described in (A) Comparative Example 2; (B) Comparative Example 3; (C) Example 1.

DETAILED DESCRIPTION

The flaky, colored, oxidized aluminum pigment has a high degree of color travel. For example, the pigment may have a bright, champagne to red-shade gold metallic color when viewed at 15° and a blue to white ceramic color when viewed at 110°. The color and color travel effects of these pigments are believed to arise directly from the surface morphology, which has relatively monodispersed particles of aluminum oxide on it. These particles are believed to be made of aluminum oxide of a certain crystal phase.

The surface of these oxidized aluminum pigments is rough and may allow higher loadings of organic pigment on the surface. In addition, the structured surface may shield any adsorbed organic pigments from oxygen and increase their fastness as well, especially if another protective coating is added. Furthermore, the surface of these oxidized aluminum pigments may have the added benefit of making the aluminum more water stable, less prone to gassing, and more shear stable.

In some embodiments, the oxidized aluminum pigment comprises not more than 95% by weight metallic aluminum, wherein the pigment is flaky. The pigment has a color travel from the hue angle range of about 50° to about 100° at the aspecular observation angle of 15°, to a hue angle range of about 200° to about 270° at the aspecular observation angle of 110°.

In some embodiments, the pigment consists of a flaky aluminum core that is coated with a structured oxide layer. This structured oxide layer comprises aluminum oxide particles containing aluminum oxide and/or hydrous aluminum oxide ($Al_2O_3$ or $Al(OH)_3$) particles. These aluminum oxide particles are on the surface of the pigment. Generally, the size, polydispersity, and spacing of the aluminum oxide particles depend on the reaction conditions. In some embodiments, the size of the aluminum oxide particles is from about 50 nm to about 400 nm, such as about 70 nm to about 350 nm, or about 150 nm to about 300 nm. Without being bound to the theory, it is believed that this structured oxide layer is responsible for the color travel observed. The structured oxide acts as kind of diffraction grating, scattering blue light at high observation angles.

In some embodiments, the aluminum oxide particles are about 5% to about 50% of the total mass of the pigment, such as about 10% to about 30%, or about 15% to about 20% of the total mass of the pigment. In some embodiments the pigment is oxidized so that the total aluminum oxide present is in the range of about 5 to about 70%, such as about 15% to about 60%, or about 20 to about 55% with respect to the total pigment weight. In general it appears that pigments with more oxidation have a larger color travel, and are more red in color at the 15° observation angle and more white at the 110° observation angle, and less brilliant in brightness than less oxidized pigments. In general, it appears that the pigments with less oxidation are more champagne in color at the 15° observation angle and more blue in color at the 110° observation angle, and more brilliant in brightness.

In some embodiments, the pigment has an average diameter ($D_{50}$) in the range of about 1 μm to about 500 μm, such as about 4 to about 100 μm, or about 9 to about 30 μm. The thickness of the pigment is in the range of about 10 nm to about 5 μm, such as about 100 nm to about 3.5 μm, or about 500 nm to about 2 μm.

The pigment is a flaky, oxidized aluminum pigment. In some embodiments, the morphology of the flaky pigment may be a cornflake or a silver dollar. In some embodiments, the morphology of the flaky pigment is a cornflake. In some embodiments, the morphology of the flaky pigment is a silver dollar. In some embodiments, the starting flaky aluminum pigment is produced by a vacuum metalized flake process (VMP).

The color travel of the oxidized aluminum pigment generally progresses from a hue angle range of about 50° to about 100° at the aspecular angle of 15° to a hue angle range of about 200° to about 270° at the aspecular angle of 110°. In some embodiments the color of the pigment is approximately a bright, champagne to red-shade gold color when viewed at the aspecular angle of 15°, and approximately a blue to white ceramic color when viewed at the aspecular angle of 110°.

In some embodiments, the CIELAB a* and b* values of the pigment viewed at a 15° aspecular angle are in the range of $-1.0 \leq a^* \leq 10.0$ and $0.0 \leq b^* \leq 25$. In some embodiments, the CIELAB a* and b* values of the pigment viewed at a 110° aspecular angle are in the range of $-10.0 \leq a^* \leq -0.5$ and $-20.0 \leq b^* \leq -2.0$.

The color of the pigment depends upon the light source and the angle of the light source. When the color of the pigment is described herein, unless clearly to the contrary, it is measured using the refinish paint system described in the examples. The measured color is converted to CIELAB coordinates for CIE standard illuminant D65, and has an illumination incident angle of 45°.

In some embodiments, the pigment is an aluminum alloy pigment. The total weight of the non-aluminum metal is present in an amount of about 0.1% to about 10% by weight of the aluminum alloy, such as about 1% to about 8%, about 3% to about 7%, or about 5%. Examples of non-aluminum metals include, but are not limited to, vanadium, iron, manganese, copper, zinc, chromium, nickel, cobalt, silicon, magnesium, titanium, and mixtures thereof. In embodiments where an aluminum alloy pigment is used, the composition of the oxide layer will comprise an oxide of aluminum and the alloyed metal.

In some embodiments, the pigment may be chemically stabilized. Examples of chemical stabilization include encapsulation with a protective layer. Examples of a protective layer include, but are not limited to, an anticorrosive layer. In some embodiments, the protective layer comprises an inorganic metal oxide, a polymeric resin, a coating of small molecules, or mixtures thereof. The protective layer is added in a subsequent step after oxidation and is located on the surface of the pigment. In some embodiments, the protective layer at least partially encapsulates the pigment. In some embodiments, the protective layer fully encapsulates the pigment.

Examples of protective layers include, but are not limited to, silicon dioxide, aluminum oxide, zirconium oxide, cerium oxide, polymeric stabilizers, inorganic phosphates, phosphate esters, organic phosphites, inorganic phosphites, organic borates, inorganic borates, fatty acids, and mixtures thereof. In some embodiments, protective layers are selected from silicon dioxide, polymeric stabilizers, and phosphate esters.

The oxidized aluminum pigments have an excellent appearance with respect to their metallic character, color travel and hiding power. As such they are useful in a number of different applications where metallic or aluminum pigments are desirable. Examples include, but are not limited to: coatings, such as interior and exterior decorative coatings (for wood, plastic and other substrates), varnish, lacquer, paint, powder coating, coil coating, industrial coating, protective and maintenance coatings, architectural coatings, automotive coating (such as refinish, OEM, interior and wheel coatings); inks such as lithographic, lithographic offset, flexographic, energy curable inks, gravure, writing ink, and screen ink; colored concrete; seed coatings; as a colored inclusion in plastics, glass, ceramics; textiles; and cosmetics, including, mascara, nail lacquer, eye shadow, eye liner, foundation, concealers, hair gel, hair spray, shampoo, lotions, blush, rouge, and soaps.

Coating Compositions

Coating compositions may be obtained by blending the oxidized aluminum pigment into a paint, ink, or other base. Both water and organic solvent-based systems can be used as the paint or the ink. The amount of the oxidized aluminum pigment in the coating composition is in the range of about 0.1% to about 35%, such as about 1% to about 20%, or about 5% to about 18%, by weight with respect to the other components of the coating system.

In some embodiments, the coating composition is obtained by blending the oxidized aluminum pigment with a coating resin. Examples of coating resins include, but are not limited to: polyester, polyurethane, polyvinyl, cellulose, polyamide, nitrocellulose, acrylic, alkyd, fluoro resins, and mixtures thereof.

In some embodiments, one or more colored pigments, effect pigments, extenders or dyes can be employed in addition to the oxidized aluminum pigment in a coating composition. Illustrative examples of the color pigment include, but are not limited to: phthalocyanine, iron oxide, quinacridone, perylene, isoindoline, azo lake, chrome yellow, carbon black, and titanium dioxide. Illustrative examples of the effect pigment include, but are not limited to: flake-form pigments of pearlescent mica, aluminum, brass, copper, silica, aluminum oxide and the like.

In some embodiments, a crosslinker, water, an organic solvent, an interfacial active agent, a hardener, an ultraviolet absorber, a thickener, as well as other additives known in the art can be included in the coating composition.

In some embodiments, a film may be formed from a coating composition by depositing the film onto a base coat layer or the like, while a topcoat layer may be further formed on the film prepared for the coating composition.

Powder Coating

Powder coating compositions may be obtained by blending the oxidized aluminum pigment into a powder base. The amount of the oxidized aluminum pigment in the powder coating composition is in the range of about 0.1% to about 15%, such as about 1% to about 10%, or about 3% to about 8%, by weight with respect to the other components of the coating system.

The powder coating composition may be obtained by blending the oxidized aluminum pigment with a thermosetting or a thermoplastic powder coating resin. Examples of the types of powder coating resins that can be used include, but are not limited to: polyester, polyurethane, polyacrylate, polyolefin, epoxy, polyamide, poly(vinyl chloride), and poly(vinylidene fluoride), as well as any acrylic, alkyd, fluoro resins, and the blends thereof.

In some embodiments, the powder coating composition may comprise a colored pigment, effect pigment, extender or dye, in addition to the oxidized aluminum pigment. Illustrative examples of the color pigment include, but are not limited to: phthalocyanine, iron oxide, quinacridone, perylene, isoindoline, azo lake, chrome yellow, carbon black, and titanium dioxide. Illustrative examples of the effect pigment include, but are not limited to: flake-form pigments of pearlescent mica, aluminum, brass, copper, silica, aluminum oxide and the like.

In some embodiments, the powder coating composition may be made by blending, bonding, or extruding, the oxidized aluminum pigment with a powder coating resin according to methods known to those skilled in the art.

In some embodiments, a crosslinker, an interfacial active agent, a hardener, an ultraviolet absorber, a thickener, a flow aid, as well as other additives known in the art can be included in the coating composition.

In some embodiments, a film may be formed with the powder coating composition by deposited the film onto a base coat layer or the like, while a topcoat layer may be further formed on the film prepared for the powder coating composition.

In some embodiments, the powder coating composition may be annealed at a temperature above the glass transition of the powder coating resin according to methods known to those skilled in the art.

Cosmetic Preparation

Cosmetic preparation showing excellent color travel, and metallic effect may be obtained by blending the oxidized aluminum pigment with a suitable base. Standard aluminum pigments tend to display only a single color, limiting the number of possible cosmetic applications. The excellent color travel displayed by the oxidized aluminum pigment described herein makes them superior compared to other aluminum pigments for use in cosmetics.

The types of cosmetic that the oxidized aluminum pigment can be blended into are not particularly limited. Examples of the embodiments of cosmetics comprising the oxidized aluminum pigments include, but are not limited to: nail lacquer, eye shadow, blush, eye liner, foundation, hair gel, hair spray, shampoo, lotions, and soaps. The amount of the oxidized aluminum pigment in a cosmetic composition can be in the range of about 0.1% to about 99%, such as about 1% to about 80%, about 1% to about 50%, about 1% to about 25%, or about 1% to about 15% by mass.

The oxidized aluminum pigment can be incorporated into cosmetic formulations as described above by methods known to those skilled in the art.

Colorant in Plastic

The oxidized aluminum pigment may be used as a colorant or additive in plastic films or articles. The amount of the oxidized aluminum pigment in plastic films or articles is in the range of about 0.1% to about 10%, such as about 0.5% to about 4%, or about 1% to about 3% by weight with respect to the other components of the plastic film or article.

In some embodiments, the plastic film or article may be obtained by blending the oxidized aluminum pigment with the plastic. Suitable plastics for the incorporation of the oxidized aluminum pigment can be any common plastic known to those skilled in the art. Examples of the types of plastics that can be used include, but are not limited to: polypropylene, polyethylene, polyester, polyurethane, polyacrylate, polyolefin, epoxy, polyamide, poly(vinyl chloride), and poly(vinylidene fluoride), as well as any acrylic, alkyd, fluoro polymers, and blends thereof.

In some embodiments, the plastic film or article may comprise a colored pigment, effect pigment, extender, or dye, in addition to the oxidized aluminum pigment. Illustrative examples of the color pigment include, but are not limited to: phthalocyanine, iron oxide, quinacridone, perylene, isoindoline, azo lake, chrome yellow, carbon black, and titanium dioxide. Illustrative examples of the effect pigments include flake-form pigments of pearlescent mica, aluminum, brass, copper, silica, aluminum oxide and the like.

Preparation of Pigment

The oxidized aluminum pigment is produced using an inverse emulsion system (water-in-oil). In general the reaction procedure involves the formation of an emulsion by admixing a biphasic liquid system consisting of an organic phase (oil phase) and an aqueous phase in the presence of a surfactant. A base is also mixed with the emulsion. The starting aluminum pigment is predominantly in the hydrocarbon solvent. In some embodiments, the emulsion in the oxidation step may additionally comprise a thickener. The aqueous phase may comprise deionized water and a base.

The oxide particles are generated through the oxidation of the surface by the following equations:

$$2Al_{(s)} + 3H_2O \rightarrow Al_2O_{3(s)} + 3H_{2(g)} \quad (1)$$

$$2Al_{(s)} + 6H_2O \rightarrow Al(OH)_{3(s)} + 3H_{2(g)} \quad (2)$$

In some embodiments, the organic and aqueous phases can be heated to make the emulsion and carry out the oxidation reaction. If the reaction is heated, the aqueous and organic phases are optionally heated to the same temperature before combining them. Suitable temperatures for the reaction are in the range of about 10° C. to about 80° C., such as from about 15° C. to about 65°, from about 20° C. to about 60°, or from about 25° C. to about 55° C. The emulsion may be made using any stirring speed that is suitable for making a water/oil emulsion.

In some embodiments, the hydrocarbon solvent of the organic phase comprises isoparaffinic hydrocarbons. In some embodiments, the hydrocarbon solvent comprises at least 50% by total weight of the reaction system. Examples of appropriate hydrocarbon solvents are: mineral spirits, mineral oil, toluene, hexane, cyclohexane, fuel oil, kerosene, and mixtures thereof.

In some embodiments, a thickener is used in the oxidation step. The thickener may be added to increase the viscosity of the organic phase and stabilize the emulsion from quickly separating. It is not added in an amount that causes the emulsion to become overly viscous. The thickener may comprise, for example, any waxes that are known to those in the art such as paraffin wax, carnauba wax, carnelian wax, and any other waxes known to those skilled in the art. In some embodiments, the thickener is added in a range of about 0% to about 15%, such as about 4% to about 10%, or about 5% to about 7%.

The surfactant may comprise any surfactant or mixture of surfactants suitable for making inverse emulsions. If no surfactant is used, the emulsion does not form and the reaction proceeds uncontrollably. Examples of surfactants suitable are those that are useful for making an inverse emulsion and have HLB (hydrophilic lipophilic balance) values in the range of about 1 to about 10, such as about 3 to about 7, or about 4 to about 5, or about 4. The surfactant may comprise pure or mixtures of cationic, anionic, zwitterionic and/or nonionic surfactants. Representative examples include, but are not limited to: lecithins (such as ADM 500®, Yelkin SS®, ADM 2100®), fatty acids, fatty amines, phosphonic acids, phosphatidylcholine, sorbitan trioleate, sorbitan tristearate, sorbitan sesquioleate, glyceryl monostearate, sorbitan monooleate, sorbitan monostearate, sorbitan monopalmitate, sorbitan monolaurate, and other surfactants known to those skilled in the art. The concentration of surfactant added is important to the overall reaction. The amount of surfactant used in the reaction is, for example, in the range of about 5% to about 20% by the total weight of the reaction, such as in the range of about 7% to about 15%. In some embodiments, more than one surfactant is used in the oxidation step as a stabilizing reagent.

The oxidized aluminum pigments are made from un-oxidized, flaky aluminum pigments. The un-oxidized aluminum pigments may be produced by milling aluminum powder, by PVD methods, or other methods, which are well known to those skilled in the art. The initial un-oxidized aluminum pigments are silver in color, and the color of the pigment is changed during the oxidation process. The type of flake used can be of the cornflake, semi-silver dollar/metallic, silver dollar, shear stable or VMP grades. The type of flake used as the starting material directly affects the appearance of the final product with respect to brilliance and degree of color travel, but not with respect to hue angles.

The starting aluminum pigment may be any type of aluminum, flaky pigment that can be used for decorative coatings and cosmetics, including leafing and non-leafing cornflake, silver dollar, and VMP flakes. A cornflake shaped pigment has an irregular flake surface and shape. A silver dollar shaped pigment is smooth, round or almost round, and has relatively smooth edges. A silver dollar shaped pigment generally has lower non-specular reflections. A VMP shaped pigment has exceptionally smooth surface and uniform flake thickness, and depending on the way they are made may have different shapes. The diameter and thickness of the starting aluminum pigment is not critical. In some embodiments, the starting aluminum pigment has an average diameter ($D_{50}$) in the range of about 1 µm to about 500 µm, such as about 6 µm to about 60 µm. In some embodiments, the average thickness of the starting aluminum pigment is in the range of about 50 nm to about 5 µm, such as about 400 nm to about 1 µm. In some embodiments, the starting aluminum pigment is in paste or powder form. In some embodiments, the paste form has been pasted with mineral spirits.

In some embodiments, the starting aluminum pigment is unalloyed and consists of >95% aluminum. In other embodiments, the starting aluminum pigment is alloyed aluminum having an alloy constituent concentration of about 0.1% to about 10% by weight of the aluminum alloy, such as about 1% to about 8%, about 3% to about 7%, or about 5%. Suitable metals for use as alloying constituents include, but are not limited to: iron, manganese, copper, vanadium, chromium, titanium, nickel, cobalt, silicon, lithium, magnesium, and/or zinc. When an alloyed aluminum pigment is used, the resultant oxidized pigment will have a metal composition that is similar to the un-oxidized starting pigment.

In some embodiments, the starting aluminum pigment is added to the oxidation step in the range of about 5% to about 40%, such as about 7% to about 20%, or about 10% to about 15% of the total weight of the reaction mixture. The starting aluminum pigment may be added prior to or after the emulsion is made.

In some embodiments, the aqueous phase is added to the hydrocarbon solvent (oil phase). As an example, deionized water may be added to the oxidation step in excess, and is sufficient to react 100% of the aluminum by Equation 1. Deionized water is typically added at about 5% to about 30%, such as about 7% to about 20%, or about 10% to about 15% of the total weight of the reaction mixture.

The base comprises a water soluble, weak base and is added to catalyze the oxidation step. Examples of a weak base include, but are not limited to: any aromatic or aliphaitic amine, alcohol amine or an inorganic base; including hydrazine, ethylamine, diethylamine, triethylamine, n-propylamine, 1-propyulamine, isopropylamine, n-butylamine, 1-butylamine, n-octylamine, 1-octylamine, ethylenediamine, ethanolamine, diethanolamine, triethanolamine, 3-amino-1-propanol, 1-amino-2-propanol, pyridine, lysine, arginine, histidine, EDTA, trisodiumphosphate, disodiumphosphate, sodium carbonate, sodium acetate and the like. In some embodiments, the base is added in the range of up to about 5%, such as about 0.1% to about 1%, or about 0.5% to about 1% of the total weight of the reaction.

In some embodiments, the oxidation step is initiated by the addition of the aqueous phase to the organic phase, in which the starting aluminum pigment is dispersed. Alternatively, the starting aluminum pigment may be added to an already made emulsion. The progress of the reaction can be followed by monitoring the production of hydrogen gas or by observing the exotherms during the reaction. The oxidation step usually starts with a short induction period followed by a period of slow hydrogen gas generation, which is accompanied by a small increase in the reaction temperature. The reaction is mostly over once the hydrogen ceases to be produced and the temperature begins to decrease. After this time, hydrogen gas generation is extremely slow and the reaction products can be filtered and washed to remove the excess solvents and reagents. In some embodiments, the length of time that the oxidation step is carried out is in the range of about 4 hours to about 12 hours, such as about 5 to about 9 hours.

The amount of oxidation of the pigment may be controlled by adjusting the amount of reagents used, such as base, water, surfactant, and aluminum pigment. Increasing the amount of base or water will generally increase the amount of oxidation. Increasing the amount of surfactant generally decreases the rate of oxidation.

Without being bound to the theory, it is believed that the size of the oxidized particles is dependent upon the characteristics of the emulsion. Such as, for example, it is believed that more water or base will lead to larger particles forming on the surface of the aluminum. Also, that adding more surfactant will lead to smaller particles as the size of the micelles decreases. In contrast, adding less surfactant leads to more oxidation and larger particles. Increased reaction times will create larger and a broader distribution of particle sizes, and shorter times will have smaller particles. An increase in temperature may also increase the size of the particles.

In some embodiments, after the pigment generated in the oxidation step is filtered, the resulting filter cake is washed with a water miscible solvent in order to remove any excess water in the filter cake. Examples of suitable solvents for washing the oxidized aluminum pigment after the oxidation step include ethyl acetate, ethanol, methanol, butanol, and isopropanol. The filter cake can either be dried to be stored as a powder or stored as a paste.

While the present disclosure has illustrated by description several embodiments and while the illustrative embodiments have been described in considerable detail, it is not the intention of the applicant to restrict or in any way limit the scope of the appended claims to such detail. Additional advantages and modifications may readily appear to those skilled in the art.

EXAMPLES

Example 1

An inverse, water-in-oil emulsion was made where the aluminum flaky pigment was dispersed in the oil phase. Yelkin SS® 700155 (5 g, Archer Daniels Midland Company) was added to 45 g mineral spirits and mixed until dispersed. To this solution was added to 5 g paraffin wax and 10 g dry weight of marketed product SUNMETALLIC® 1400 series pigment 819-1419 (Sun Chemical, Parsippany, USA) (D50=19 micron) in a round bottom flask equipped with a condenser and a stir bar. The temperature was raised to 50° C. and the ingredients stirred vigorously. To start the reaction, a solution of water (10 g) and 0.60 g ethylenediamine (EDA) at 50° C. was added drop-wise to the slurry. The reaction proceeded exothermically with the generated of hydrogen gas, causing foaming in the reaction flask. After four hours, the reaction was stopped, filtered, washed with mineral spirits, and finally washed with isopropanol to remove excess water. The resultant pigment is bright gold with color travel through the second quadrant to blue.

Example 2

An inverse, water-in-oil emulsion was made where the aluminum flaky pigment was dispersed in the oil phase. Yelkin SS® 700155 (10 g, Archer Daniels Midland Company) was added to 90 g mineral spirits and mixed until dispersed. This solution was added to 10 g paraffin wax and 15 g dry weight of marketed product SUNMETALLIC® 1400 series pigment 819-1419 (Sun Chemical, Parsippany, USA) ($D_{50}$=19 micron) in a round bottom flask equipped with a condenser and a stir bar. The temperature was raised to 50° C. and the ingredients stirred vigorously. To start the reaction, a solution of water (40 g) and 0.45 g ethylenediamine (EDA) at 50° C. was added drop-wise to the slurry. The reaction proceeds exothermically with the generation of hydrogen gas, causing foaming in the reaction flask. After six hours, the reaction was stopped, filtered, washed with mineral spirits, and finally washed with isopropanol to remove excess water. The resultant pigment is bright gold with color travel through the second quadrant to blue.

Examples 3-6

SUNMETALLIC® 1400 series pigment 819-1419 (15 g, Sun Chemical, Parsippany, USA) ($D_{50}$=19 micron) was oxidized according to the procedure outlined in Example 2, except the amount of EDA, reaction temperature, and water content were varied accordingly and the levels used are recorded in Table 1.

TABLE 1

EDA amount, reaction temperature and water content for Examples 2-6.

| Example | EDA added (g) | Water added (g) | Reaction Temp. (° C.) |
|---|---|---|---|
| Example 2 | 0.45 | 40.0 | 50 |
| Example 3 | 1.20 | 20.0 | 50 |
| Example 4 | 0.60 | 20.0 | 50 |
| Example 5 | 1.2 | 40.0 | 35 |
| Example 6 | 1.2 | 20.0 | 35 |

Example 7

An inverse, water-in-oil emulsion was made where the aluminum flaky pigment was dispersed in the oil phase. ADM 500® (30 g, Archer Daniels Midland Company) was added to 180 g mineral spirits and mixed until dispersed. This solution was added to 20 g paraffin wax and 30 g dry aluminum silver dollar pigment ($D_{50}$=15 micron) into a one liter reactor equipped with a condenser and a stirrer. The temperature was raised to 35° C. and the ingredients stirred vigorously. To start the reaction, a solution of water (40 g) and 1.2 g ethylenediamine (EDA) at 35° C. was added drop-wise to the slurry. The reaction proceeds exothermically with the generation of hydrogen gas, causing foaming in the reactor. After six hours, the reaction was stopped, filtered, washed with mineral spirits, and finally washed with isopropanol to remove excess water. The resultant pigment is a light brown color with color travel through the origin to blue.

Example 8

An inverse, water-in-oil emulsion was made where the aluminum flaky pigment was dispersed in the oil phase. ADM 500® (30 g, Archer Daniels Midland Company) was added to 180 g mineral spirits and mixed until dispersed. This solution was added to 20 g paraffin wax and 30 g dry weight of marketed product SUNMETALLIC® 1400 series pigment 819-1419 (Sun Chemical, Parsippany, USA) ($D_{50}$=19 micron) into a one liter reactor equipped with a condenser and a stirrer. The temperature was raised to 35° C. and the ingredients stirred vigorously. To start the reaction, a solution of water (40 g) and 1.5 g 3-amino-1-propanol (APOL) at 35° C. was added drop-wise to the slurry. The reaction proceeds exothermically with the generation of hydrogen gas, causing foaming in the reactor. After six hours, the reaction was stopped, filtered, washed with mineral spirits, and finally washed with isopropanol to remove excess water. The resultant pigment is a reddish-gold color with color travel through the origin to blue.

Example 9

An inverse, water-in-oil emulsion was made where the aluminum flaky pigment was dispersed in the oil phase. ADM 500® (40 g, Archer Daniels Midland Company) was added to 372 g mineral spirits and mixed until dispersed. This solution was added to 40 g paraffin wax and 60 g dry weight of marketed product SUNMETALLIC® 1400 series pigment 819-1419 (Sun Chemical, Parsippany, USA) ($D_{50}$=19 micron) into a one liter reactor equipped with a condenser and a stirrer. The temperature was raised to 35° C. and the ingredients stirred vigorously. To start the reaction, a solution of water (80 g) and 2.4 g ethylenediamine (EDA) at 35° C. was added drop-wise to the slurry. The reaction proceeds exothermically with the generation of hydrogen gas, causing foaming in the reactor. After six hours, the reaction was stopped, filtered, washed with mineral spirits, and finally washed with isopropanol to remove excess water. The pigment was dried at 60° C. under vacuum. The resultant pigment is gold with color travel through the origin to blue.

Comparative Example 1

The marketed product SUNMETALLIC® 1400 series pigment 819-1419 (Sun Chemical, Parsippany, USA).

Comparative Example 2

The marketed product Aloxal® Bright Champagne (Eckart, Fürth, Germany).

Comparative Example 3

Dry aluminum flaky pigment (31.5 g, $D_{50}$=19 micron, SUNMETALLIC® 1400 series pigment 819-1419 (Sun Chemical, Parsippany, USA)) was added to 118 g isopropanol in a reactor and stirred with a mechanical stirrer. The mixture was heated to reflux. Water (11 g) and 0.60 g ethylenediamine were added to the reactor. After about 90 minutes, hydrogen production was observed. Generation of hydrogen gradually became more vigorous. After about 3 hours, the majority of the hydrogen production was over and the reaction was cooled to room temperature. The pigment was filtered and washed with copious amounts of isopropanol and stored as a paste.

Example 10

Evaluation of the Pigments

Figure 1A:
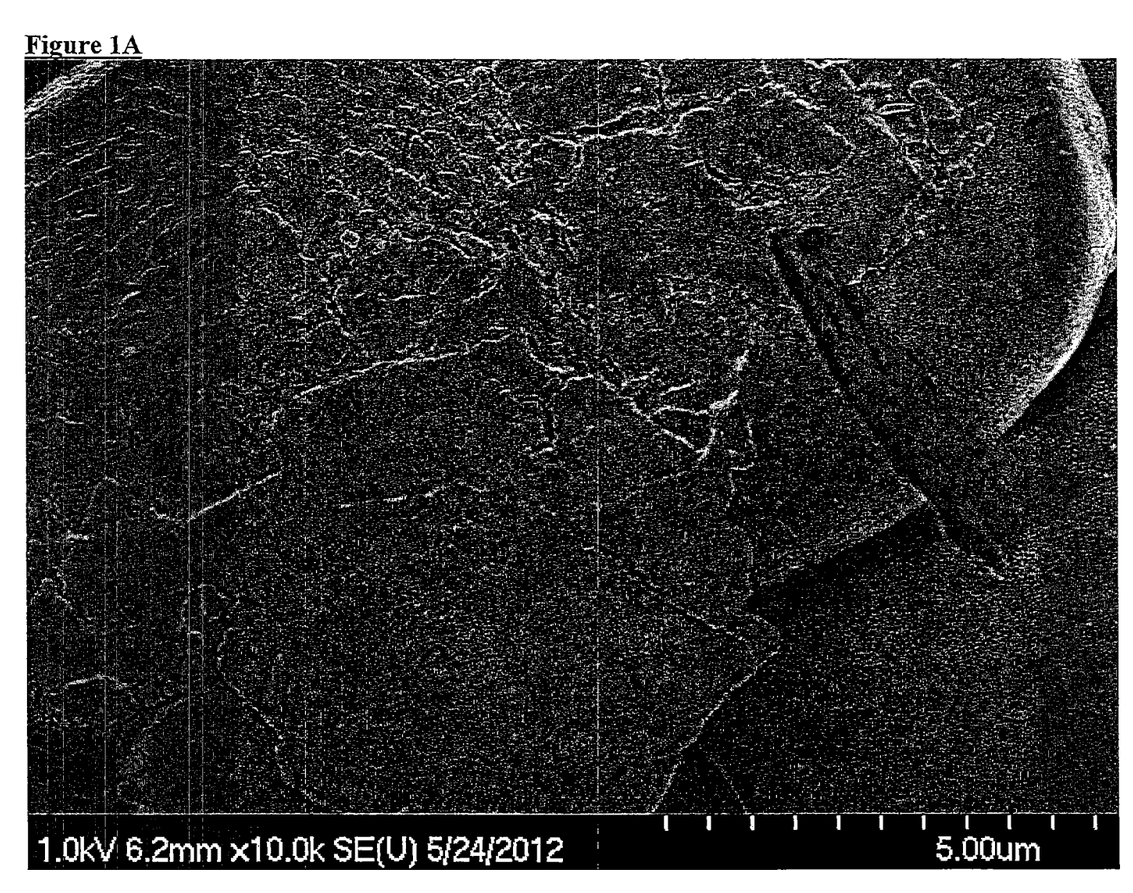
Figure 1B:
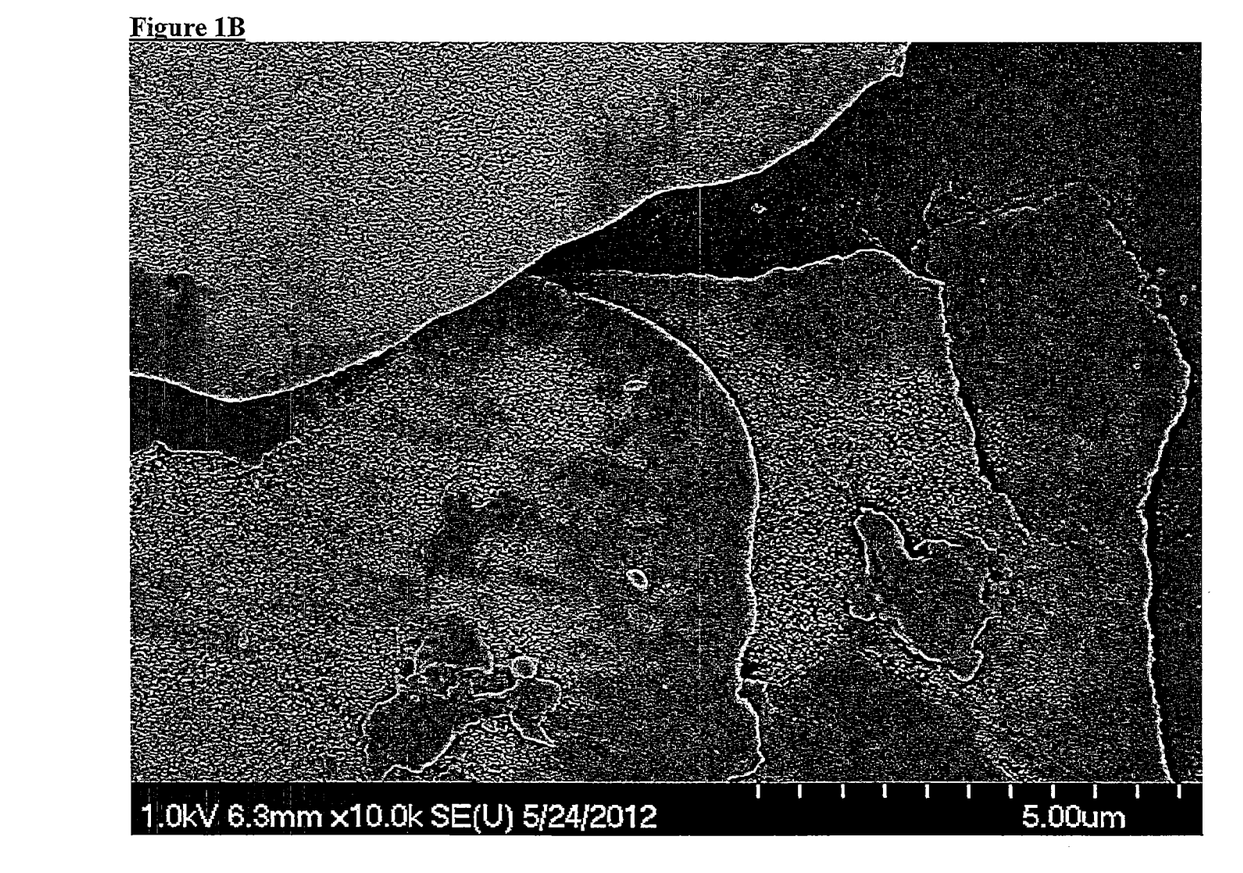
Figure 1C:
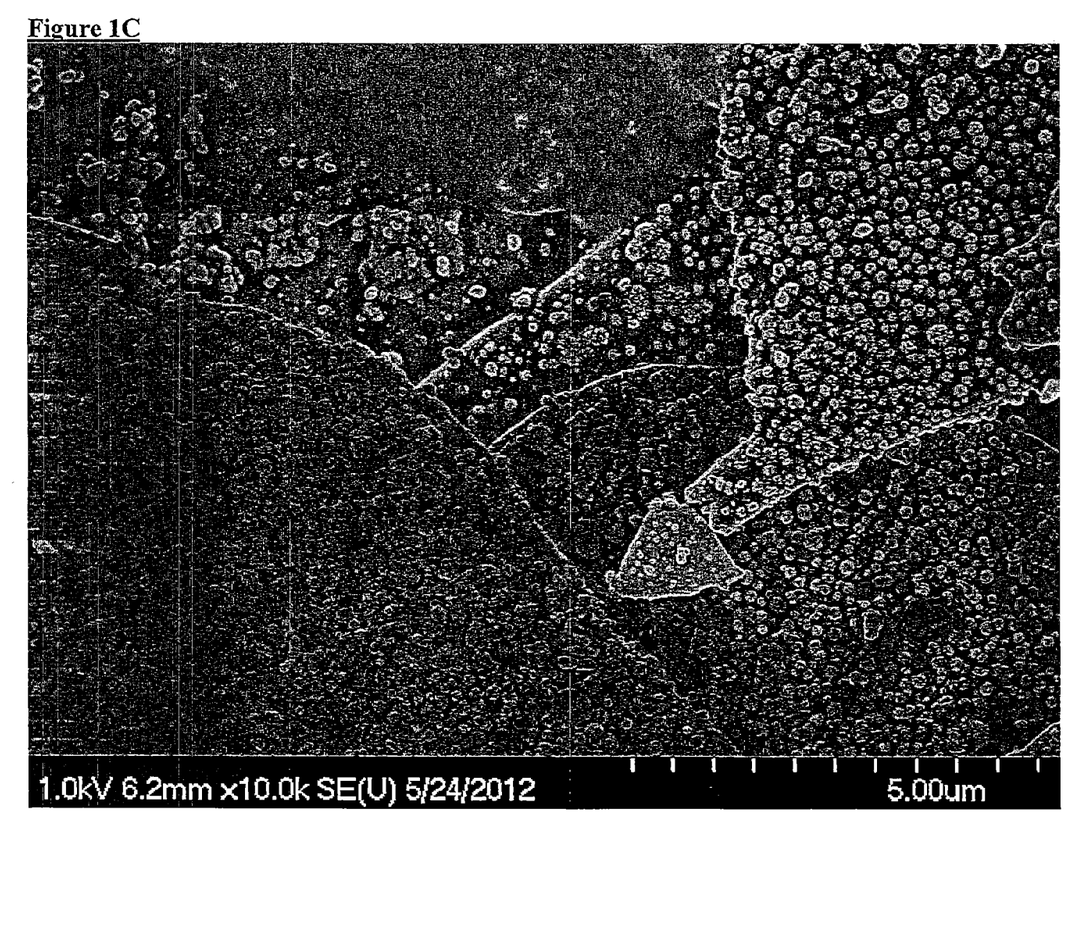

FIGS. 1A, B and C show representative scanning electron microscope (SEM) micrographs of the oxidized aluminum pigments from Comparative Examples 2 and 3 and Example 1, respectively. These micrographs show that the oxidized aluminum pigments in Comparative Examples 2 and 3 both a have porous structures caused by the direct oxidation of their surface. In contrast, the oxidized aluminum pigments of Example 1 show the presence of many spherical structures on the pigment surface. These structures are believed to act similarly to a diffraction grating and are the cause of the extreme color travel observed.

Refinish Paint System

The appearance of the oxidized aluminum pigments produced in Examples 1-9, and Comparative Examples 1-3, were evaluated. A pigment sample (0.8 g) was mixed in 10 g of a cellulose acetate butyrate/acrylate resin for 3 minutes using a Speedmixer (DAC150FVZ-K) from FlackTeck, Inc. Samples were doctor-bladed using a #3 Byrd applicator on a piece of black and white cardboard. After the film had dried, CIELAB values were measured with an X-Rite MA-98 multiangle spectrophotometer at an incident angle of 45° and at aspecular angles of 15°, 25°, 45°, 75°, and 110° using standard illuminant D65.

Figure 2:
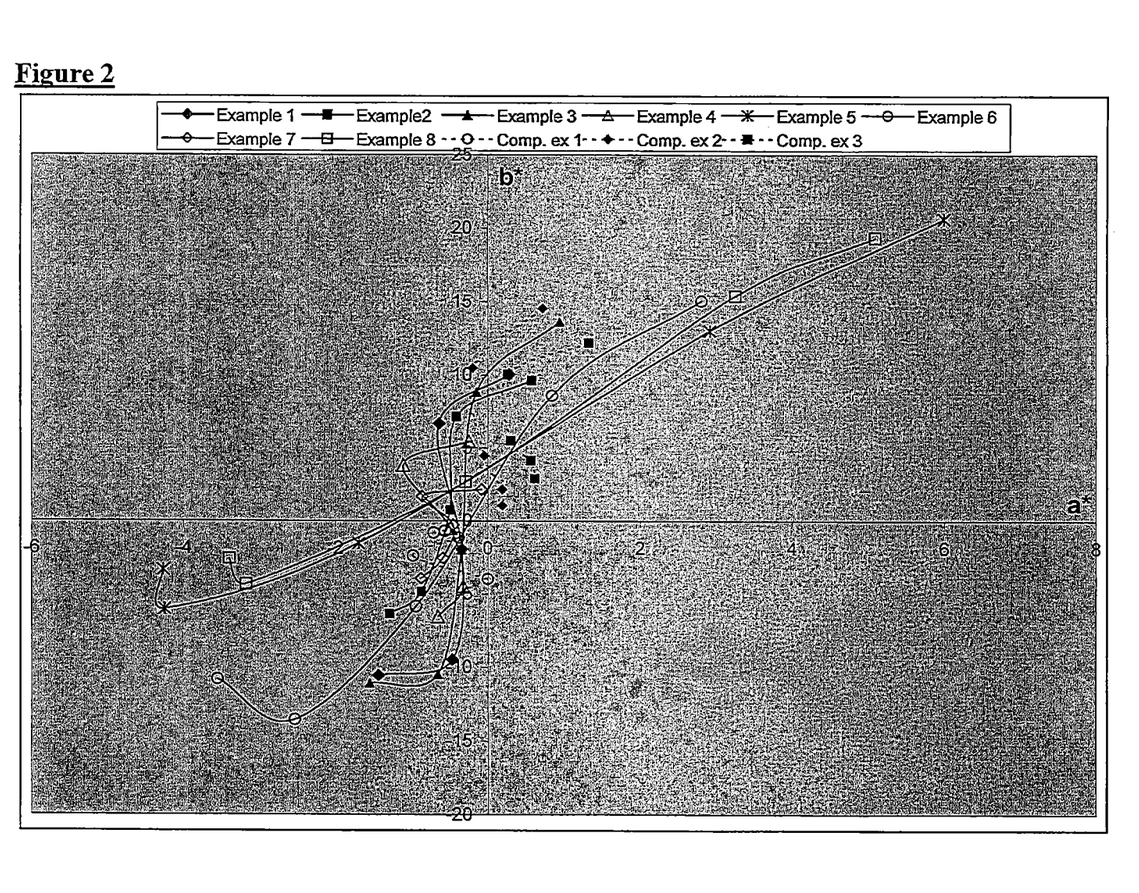
FIG. 2: Graph of color travel in CIELAB color space for the pigments described in Examples 1-8 and Comparative Examples 1-3.

The effect lines of the pigments described in Examples 1-8 and Comparative Examples has been plotted in FIG. 2. Comparative Example 1 is a standard silver dollar aluminum pigment and its color travel remains in the achromatic region of CIELAB color space. In contrast, the color travel of the oxidized pigments of Comparative Examples 2 and 3 lies in the first quadrant and the effect line tends towards the origin at 110°. This type of behavior is typical for most interference colors, and suggests that the color for Comparative Examples 2 and 3 depends on the thickness of the oxidized layers on their surfaces.

The pigments described in Examples 1-8 display a much different behavior from the comparison examples. At low observation angles, such as around 15° to 25°, the color of the pigments is generally in the first quadrant, but as the observation angle of the pigments increases, such as around 75° to 110°, the color moves into the third quadrant. The effect line in FIG. 2 shows travel from around the first quadrant to the third quadrant. This type of color travel is believed to be due to the structured oxide surface of the pigments described. The structured surface acts as a type of diffraction grating and tends to cause the incident blue light to be reflected at high aspecular angles. Such a phenomenon has not been previously observed for flaky aluminum pigments.

Sprayed Paint Panels

Example 6 was incorporated into a solvent borne, cellulose acetate butyrate/acrylate resin for a base coat, sprayed on a stainless steel panel. The dry pigment from Example 6 (7.2 g) was dispersed in 90 g of the solvent-borne, cellulose acetate butyrate/acrylate basecoat resin and then mixed with a solvent-based thinner until the desired viscosity was achieved. The samples were sprayed onto an aluminum panel and baked in an oven at 120° C. Then an acrylic clear coat was sprayed onto the aluminum panel and baked in an oven at 120° C. The CIELAB values were measured using an X-Rite MA-98 multiangle spectrophotometer with an incident angle of 45° at aspecular angles of 15°, 25°, 45°, 75°, and 110°. The color measurements were converted to CIELAB coordinates for CIE standard illuminant D65 and are reported in Table 2. The pigment in the sprayed sample displays characteristic color travel and metallic character.

TABLE 2

CIELAB values for spray panel of Example 6 at different angles

| Measuring Angle | L* | a* | b* |
|---|---|---|---|
| 15 | 137.08 | 2.36 | 17.21 |
| 25 | 100.20 | 0.77 | 11.55 |
| 45 | 54.63 | −0.49 | −3.30 |
| 75 | 41.69 | −1.68 | −12.74 |
| 110 | 41.99 | −2.68 | −11.33 |

Powder Coating

The oxidized aluminum pigment produced in Example 9 was evaluated in a powder coating. The pigment was dry blended at a loading of 5% in a clear powder coating base. The samples were dry sprayed onto metal panels and cured in an oven set to 190° C. for 10 minutes. After the film had dried, the CIELAB values were measured using an X-Rite MA-98 multiangle spectrophotometer with an incident angle of 45° at aspecular angles of 15°, 25°, 45°, 75°, and 110°. The color measurements were converted to CIELAB coordinates for CIE standard illuminant D65 and are reported in Table 3. The pigment in the sprayed sample displays characteristic color travel and metallic character.

TABLE 3

CIELAB values for the powder spray panel of Example 9.

| Measuring Angle | L* | a* | b* |
|---|---|---|---|
| 15 | 95.88 | 1.40 | 10.16 |
| 25 | 74.63 | 0.70 | 7.96 |
| 45 | 49.89 | −0.20 | −1.83 |

TABLE 3-continued

CIELAB values for the powder spray panel of Example 9.

| Measuring Angle | L* | a* | b* |
|---|---|---|---|
| 75 | 39.58 | −1.09 | −2.83 |
| 110 | 37.17 | −1.43 | −3.30 |

Cosmetic Composition

The oxidized aluminum pigment produced in Example 8 was evaluated in a cosmetic composition. The oxidized aluminum pigment from Example 8 (0.6 g) was mixed in a 10 g nitrocellulose resin suitable for nail lacquers for 3 minutes using a Speedmixer (DAC150FVZ-K) from FlackTeck, Inc. Samples were drawn down using a #3 Byrd applicator on black and white cardboard. After the film had dried, CIELAB values were measured using an X-Rite MA-98 multiangle spectrophotometer with an incident angle of 45° at aspecular angles of 15°, 25°, 45°, 75°, and 110°. The color measurements were converted to CIELAB coordinates for CIE standard illuminant D65. The values are reported in Table 4. Pigments in the nail lacquer display characteristic color travel and metallic character.

TABLE 4

CIELAB values for drawn down nail lacquer of Example 8.

| Measuring Angle, Example 8 | L | a* | b* |
|---|---|---|---|
| 15° | 118.99 | 5.50 | 21.10 |
| 25° | 89.70 | 2.86 | 14.16 |
| 45° | 55.81 | −0.81 | 0.98 |
| 75° | 47.09 | −3.25 | −4.63 |
| 110° | 45.18 | −3.45 | −2.66 |

Incorporation into Plastic

In a 250 glass beaker, 30 g Hi-Sol 10 (Ashland Inc., Covington, USA) and 29.3 g Vestowax A 235 (Evonik Industries, Germany) were mixed at 105° C. until uniform. The resultant mixture was blended with 68.4 g of the dry pigment from example 9 and 74.8 g isopropanol in a dual arm mixer that has been pre-warmed to 80° C. in an oven. Isopropanol (40 g) was added to the mixture and stirred for 5 minutes. The mixture was then manually pushed through a screen to make pellets. The pellets were dried overnight in an oven at 80° C.

The pellets (5.5 g) were mixed in a plastic container with 1.85 g zinc stearate and 72.85 g polypropylene resin and then added to a plastic bag containing 290.0 g additional polypropylene resin. The contents of the bag were kneaded until uniform and then placed in a Battenfeld injection molder. The sample was injection molded to make polypropylene chips using techniques known to those skilled in the art at a temperature of 232° C. The plastic chips have a gold face color that shows travel to blue at oblique angles.

SEM Image Analysis

Samples of Comparative Examples 2 and 3 and Example 1, were mounted on an aluminum stub treated with a piece of double-sided, conductive carbon tape. The excess sample on the stub was removed by using pressurized air. SEM analysis was performed in a Hitachi S-4700 scanning electron microscope using an accelerating voltage of 1.0 kV and a working distance of 4 mm. The scans of Comparative Examples 2 and 3 and Example 1, are shown in FIGS. 1A-1C, respectively. The presence of ~200 nm particles are discernible on the surface of the pigment in FIG. 2C, which corresponds to Example 1 of the present invention.

Example 11

An inverse, water-in-oil emulsion was made where the aluminum flaky pigment was dispersed in the oil phase. ADM 500® (80 g, Archer Daniels Midland Company) was added to 744 g mineral spirits and mixed until dispersed. This solution was added to 80 g paraffin wax and 120 g dry weight of SUNMETALLIC® 1400 series pigment 819-1419 (Sun Chemical, Parsippany, USA) ($D_{50}$=19 micron) into a two liter reactor equipped with a condenser and a stirrer. The temperature was raised to 40° C. and the ingredients stirred vigorously. To start the reaction, a solution of water (160 g) and 4.8 g ethylenediamine (EDA) at 40° C. was added drop-wise to the slurry. The reaction proceeded exothermically with the generation of hydrogen gas, causing foaming in the reactor. After seven hours, the reaction was stopped, filtered, washed with mineral spirits, and finally washed with isopropanol to remove excess water. The resultant pigment is gold with color travel through the origin to blue.

Example 12

Addition of a Stabilizing Layer

A one liter reactor was loaded with 116.45 g of the pigment from Example 11 and 617 g isopropanol, stirred and brought to reflux. Tetraethoxysilane (35.4 g) was added to the reactor. A separate solution of 63 g deionized water and 9.9 g 25% ammonia was added to the reactor over a period of three hours. Finally, 3.5 g 3-aminopropyltrimethoxysilane was added and the mixture was stirred for 2 additional hours. The reaction was cooled, filtered, and washed with isopropanol. The stabilized pigment has a similar color to the pigment from Example 11.

Evaluation of the Color

The appearance of the oxidized aluminum pigment produced in Example 11, and the stabilized oxidized aluminum pigment of Example 12 was evaluated. A pigment sample (0.8 g) was mixed in 10 g of a cellulose acetate butyrate/acrylate resin for 3 minutes using a Speedmixer (DAC150FVZ-K) from FlackTeck, Inc. Samples were doctor-bladed using a #3 Byrd applicator on a piece of black and white cardboard. After the film had dried, CIELAB values were measured using an X-Rite MA-98 multiangle spectrophotometer with an incident angle of 45° at aspecular angles of 15°, 25°, 45°, 75°, and 110°. The color measurements were converted to CIELAB coordinates for CIE standard illuminant D65. The results of the color evaluation are shown in Table 5. The chemically stabilized pigment of Example 12 has very similar color measurements to the oxidized aluminum pigment of Example 11. This suggests that chemical stabilization does not affect the color travel of the oxidized aluminum pigment.

TABLE 5

CIELAB values for Examples 11 and 12.

| Measuring Angle | Example 11 | | | Example 12 | | |
|---|---|---|---|---|---|---|
| | L | a* | b* | L | a* | b* |
| 15° | 123.62 | 2.20 | 14.73 | 122.47 | 2.22 | 14.76 |
| 25° | 98.31 | 1.10 | 12.19 | 96.22 | 1.06 | 11.94 |
| 45° | 62.22 | −0.16 | 2.47 | 60.85 | −0.24 | 2.13 |
| 75° | 45.67 | −1.52 | −6.47 | 45.21 | −1.52 | −6.48 |
| 110° | 42.48 | −2.07 | −7.62 | 42.02 | −2.05 | −7.55 |

Evaluation of Pigment Stability

To test the water stability of the pigments produced in Examples 11, 12 and Comparative Example 1, a gassing test was carried out to measure the amount of hydrogen produced when the pigment was introduced to a mildly caustic aqueous system. Into a 100 mL round bottom flask was weighed 10 g isopropanol and 1 g pigment. The sample was stirred and heated to 60° C. Sodium borate solution (25 mL of a 0.01 M solution) was added to the round bottom flask. The flask was immediately connected to a reservoir containing water. As the sample released hydrogen gas due to oxidation, the water in the reservoir was displaced. The amount of water displaced into a graduated cylinder was measured over the course of the test.

Table 6 shows that the unpassivated oxidized aluminum pigment of Example 11 and the unpassivated aluminum pigment of Comparative Example 1 behave similarly, releasing more than 250 mL of gas in less than 1 hour. The stabilized pigment of Example 12 shows markedly less gassing over the entire 7 hour period of the test. This data combined with the color data, shows that the pigments can be passivated leading to reduced gassing in aqueous systems.

TABLE 6

Results of the gassing test for Examples 11-12

| Sample | Amt. gassed (mL) | Time gassed (hours) |
|---|---|---|
| Comparative Example 1 | 250 | 0.9 |
| Example 11 | 250 | 0.2 |
| Example 12 | 72 | 7 |

Those skilled in the art having the benefit of the teachings of the present invention as hereinabove set forth, can effect numerous modifications thereto. These modifications are to be construed as being encompassed within the scope of the present invention as set forth in the appended claims.

What is claimed is:

1. An oxidized aluminum pigment comprising not more than 95% by weight metallic aluminum, wherein the pigment has aluminum oxide particles with a diameter from about 50 nm to about 400 nm on the surface of the pigment.

2. The pigment of claim 1, wherein the pigment is a flaky particle, and exhibits a color travel with a hue angle range of about 50° to about 100° at the aspecular angle of 15° to a hue angle range of about 200° to about 270° at the aspecular angle of 110°.

3. An oxidized aluminum pigment comprising not more than 95% by weight metallic aluminum, wherein the pigment is a flaky particle, and exhibits a color travel with a hue angle range of about 50° to about 100° at the aspecular angle of 15° to a hue angle range of about 200° to about 270° at the aspecular angle of 110°.

4. The pigment of claim 1, wherein the pigment has an average diameter ($D_{50}$) in the range of about 1 μm to about 500 μm and a thickness between about 10 nm and about 5 μm.

5. The pigment of claim 1, wherein the total aluminum oxide is about 5% to about 70% with respect to the total pigment weight.

6. The pigment of claim 1, wherein the pigment has either a cornflake, or a silver dollar morphology.

7. The pigment of any one of claim 1, wherein the aluminum pigment is a made by VMP.

8. The pigment of claim 1, wherein the CIELAB a* and b* values at a 15° aspecular angle are in the range of $-1.0 \leq a^* \leq 10.0$ and $0.0 \leq b^* \leq 25$.

9. The pigment of claim 1, wherein the CIELAB a* and b* values at a 110° aspecular angle are in the range of $-10.0 \leq a^* \leq -0.5$ and $-20.0 \leq b^* \leq -2.0$.

10. The pigment of claim 1, wherein the pigment is an oxidized aluminum alloy pigment, wherein the aluminum alloy comprises at least one non-aluminum metal, wherein the total weight of non-aluminum metal is more than 5% by weight of the aluminum alloy, wherein the non-aluminum metal comprises one or more from the following group of vanadium, iron, manganese, copper, zinc, chromium, nickel, cobalt, silicon, magnesium, and titanium.

11. The pigment of claim 1, which is chemically stabilized by encapsulation with a protective layer.

12. A coating composition, comprising the pigment of claim 1, wherein the composition is selected from interior and exterior decorative coatings, varnish, lacquer, paint, powder coating, coil coating, industrial coating, protective and maintenance coatings, architectural coatings, and automotive coating.

13. A cosmetic comprising the pigment of claim 1, wherein the cosmetic is selected from nail lacquer, eye shadow, blush, eye liner, foundation, hair gel, hair spray, shampoo, lotions, and soaps.

14. A method of making an oxidized aluminum pigment of claim 1 comprising the steps of:
    providing a flaky aluminum pigment, and
    oxidizing the aluminum pigment in a water-in-oil emulsion in the presence of a base;
    wherein the water-in-oil emulsion comprises a mixture of water, a hydrocarbon solvent, and a surfactant;
    wherein the aluminum pigment is predominantly in the hydrocarbon solvent during the oxidation step, and the amount of water in the mixture is in the range of about 5% to about 40% of the total weight of the emulsion.

15. The method of claim 14, wherein the provided flaky aluminum pigment comprises at least 99% aluminum by weight.

16. The method of claim 14, wherein the provided flaky aluminum pigment comprises an aluminum alloy.

17. The method of claim 14, wherein the hydrocarbon solvent comprises at least one compound selected from mineral spirits, mineral oil, hexane, toluene, cyclohexane, fuel oil, kerosene, and mixtures thereof.

18. The method of claim 16, wherein the base comprises at least one compound selected from hydrazine, ethylamine, diethylamine, triethylamine, n-propylamine, 1-propylamine, isopropylamine, n-butylamine, 1-butylamine, n-octylamine, 1-octylamine, ethylenediamine, ethanolamine, diethanolamine, triethanolamine, 3-amino-1-propanol, 1-amino-2-propanol, pyridine, lysine, arginine, histidine, EDTA, trisodiumphosphate, disodiumphosphate, sodium carbonate, sodium acetate, and mixtures thereof.

19. The method of claim 14, wherein during at least a portion of the oxidation step the temperature of the mixture is in range of 10° C. to 80° C.

20. The method of claim 14, additionally comprising the step of at least partially encapsulating the pigment with a protective layer.

* * * * *